(12) United States Patent
Fleischmann et al.

(10) Patent No.: US 6,375,682 B1
(45) Date of Patent: Apr. 23, 2002

(54) COLLAPSIBLE, ROTATABLE AND EXPANDABLE SPINAL HYDRAULIC PROSTHETIC DEVICE

(76) Inventors: Lewis W. Fleischmann, 9004 Pittsfield Rd., Pikesville, MD (US) 21208; Christopher Galuardi, 35 Latimore Way, Owings Mills, MD (US) 21117

( * ) Notice: Subject to any disclaimer, the term of this patent is extended or adjusted under 35 U.S.C. 154(b) by 0 days.

(21) Appl. No.: 09/922,161

(22) Filed: Aug. 6, 2001

(51) Int. Cl.[7] .................................................. A61F 2/44
(52) U.S. Cl. ................... 623/17.12; 623/17.15; 623/17.16
(58) Field of Search .................. 623/17.12, 17.15, 623/17.16, 17.11, 16.11

(56) References Cited

U.S. PATENT DOCUMENTS

| | | |
|---|---|---|
| 3,867,728 A | 2/1975 | Substad et al. |
| 3,875,595 A | 4/1975 | Froning |
| 4,904,260 A | 2/1990 | Ray et al. |
| 4,932,975 A | 6/1990 | Main et al. |
| 5,002,576 A | 3/1991 | Fuhrmann et al. |
| 5,171,278 A | 12/1992 | Pisharodi |
| 5,171,280 A * | 12/1992 | Baumgartner |
| 5,236,460 A * | 8/1993 | Barber |
| 5,458,642 A | 10/1995 | Beer et al. |
| 5,571,189 A | 11/1996 | Kuslich |
| 5,645,597 A | 7/1997 | Krapiva |
| 5,755,807 A | 5/1998 | Anstaett et al. |
| 6,066,154 A | 5/2000 | Reiley et al. |
| 6,113,599 A | 9/2000 | Landsberger |

* cited by examiner

Primary Examiner—Jeffrey A. Smith
(74) Attorney, Agent, or Firm—Rosenberg, Klein & Lee

(57) ABSTRACT

A spinal prosthetic device (10) which is hydraulically expanded or retracted, either pre-implantation or in-situ, thereby being adjustable for the exact intravertebral axial spacing required for the patient. Thrust bearing members (22) are positioned between the vertebra engaging members (12) and a pair of bellows (26), allowing the collapsible/expandable bellows (26) to be rotated with respect to the vertebra engaging members (12). The device (10) can be readjusted, on an out-patient basis, months after initial implantation. The spinal prosthetic device (10) offers all degrees of motion afforded by the anatomical spinal disc and by virtue of incorporating no rubbing contact of any parts, exhibits and infinite working life. The spinal prosthetic device (10) reproduces the same hydraulic load bearing capability as the nucleus pulposis and flexural freedom of movement similar to the annulus fibrosis.

27 Claims, 8 Drawing Sheets

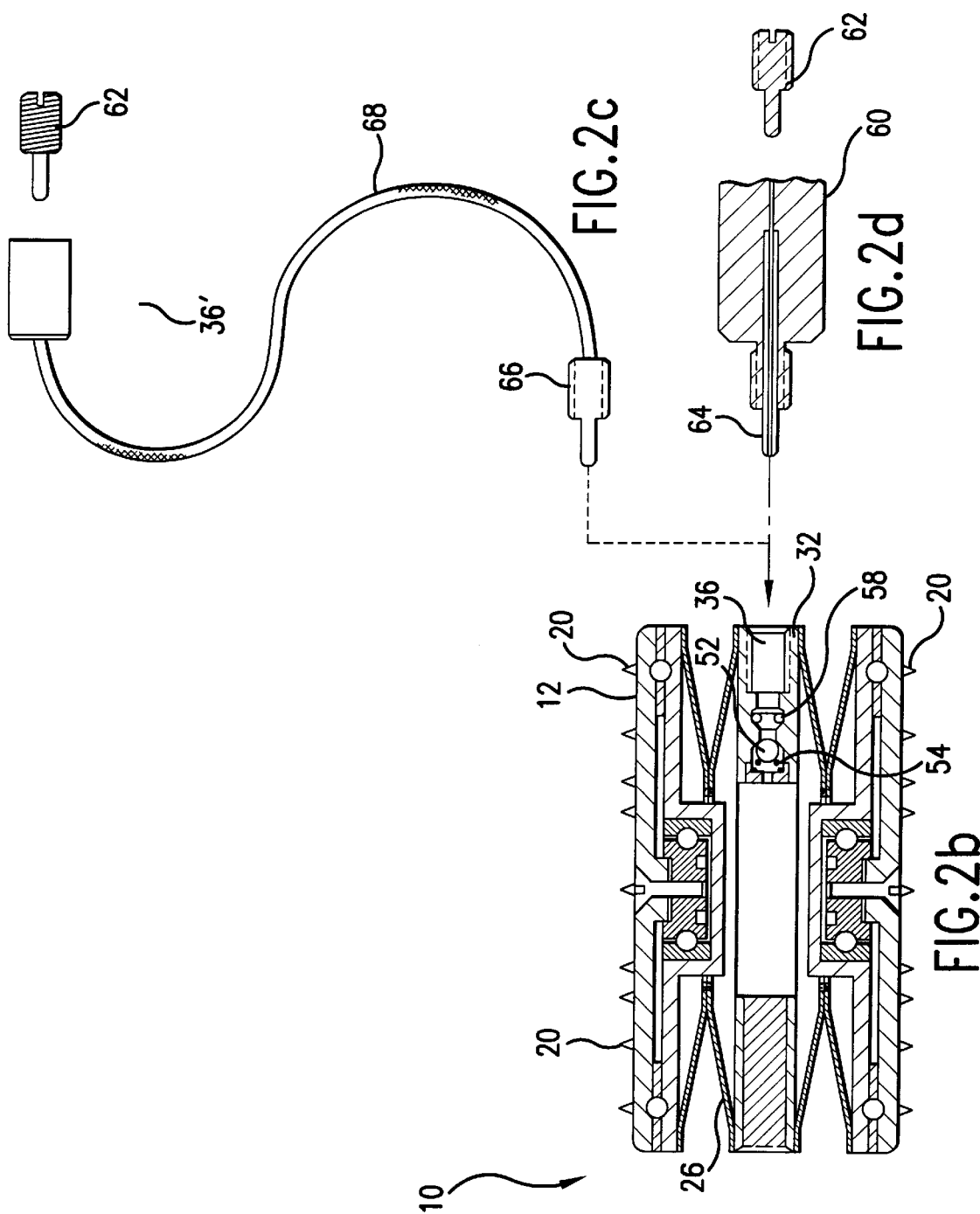

TYPICAL STRESS VS. DEFLECTION FOR METALS

COLLAPSIBLE, ROTATABLE AND EXPANDABLE SPINAL HYDRAULIC PROSTHETIC DEVICE

BACKGROUND OF THE INVENTION

1. Field of the Invention

The subject invention relates to a collapsible, rotatable and expandable spinal hydraulic prosthetic device which may be either implanted within the center of a diseased spinal disk in place of the nucleus pulposis or may replace a degenerated disk altogether. In particular, the present invention directs itself to a spinal prosthesis formed of a bio-compatible metallic bellows, the bellows being filled with a non-compressible fluid. More particularly, this invention directs itself to a spinal prosthesis having the capability of rotating between the two vertebrae adjacent the prosthesis.

Further, the bellows is formed from a plurality of rigid washer-like members, minimizing shear and movement in the lateral direction. Additionally, this invention directs itself to an implantable spinal prosthetic device having an adjustable height, either in vivo or pre-insertion, the height being adjusted to the desired intravertebral spacing of the spine.

2. Prior Art

Implantable spinal prosthetic devices are known in the art. Presently, the primary method employed to remediate degenerative disk disease, discogenic pain or spinal stenosis is through spinal fusion. In this procedure, two or more vertebrae are displaced, the spinal disks between the vertebrae are removed, and crushed bone material taken from the patient's pelvis is inserted between the two vertebrae. This bone material promotes the growth of new bone in the interstitial space between the vertebrae. Since this growth takes time, some mechanical means must be incorporated at the time of the surgery to rigidly maintain the proper spacing between the vertebrae as well as carry normal ambulatory loads imposed on the spine by the patient. Since the fused vertebrae will no longer take part in normal flexing, higher stress loads will now be imposed on the disks and the vertebrae directly above and below the fused vertebrae.

Commonly used implantable devices include semi-rigid elastomeric filler materials sandwiched between two layers of biocompatible metal. The upper and lower plate surfaces generally have multiple spikes for connection to the vertebrae. Other similar devices offer means to screw the upper and lower plates into their cojoining vertebrae and include treated plates to promote bone growth into them. These devices generally permit a small amount of articulation between the vertebrae, and the longevity of the elastomeric materials and their bonding agents are often quite short. The ideal prosthesis would last 30 to 40 years and withstand two million cycles per year.

It is a purpose of the subject invention to provide a combination of elements making up an implantable spinal prosthesis having both a long life expectancy and providing for total articulation within the spine. More particularly, the subject spinal prosthesis allows for tilting from side to side, front to back, minute elongation and compression along a main axial direction and also rotation of the prosthesis between the two vertebrae about the main axis.

One prior art spinal prosthesis is shown in U.S. Pat. No. 5,002,576. This reference is directed to an intervertebral disk endoprosthesis. This reference teaches a prosthetic device having a central elastomeric layer sandwiched between two cover plates. The prosthetic device is neither rotatable between vertebrae, nor does it provide for sufficient bending in the forward, backward or lateral directions.

Another prior art prosthetic implant is shown in U.S. Pat. No. 4,932,975. This reference is directed to a vertebral prosthesis. The device includes an initially flexible bellows and is made inflexible by injection of a fluid which solidifies and, further, does not allow for rotation between the two vertebrae.

U.S. Pat. No. 3,875,595 is directed to an intervertebral disk prosthesis and instruments for locating the same. The prosthesis is a hollow, bladder-like member having in expanded shape the appearance of the natural nucleus of a natural spinal disk. The device does not allow for rotation between vertebrae, thus not giving the user full articulated movement.

U.S. Pat. No. 5,571,189 is directed to an expandable fabric implant for stabilizing the spinal motion segment. The implant is in the form of an inflatable bag positioned within a cavity artificially formed within the spine. The inflatable bag does not provide for rotation between the vertebrae.

Another prior art prosthesis is shown in U.S. Pat. No. 5,755,807. This reference is directed to an implant module unit and rotating seal for a prosthetic joint. This implant includes a ball-and-socket joint surrounded by a flexible metallic bellows. However, the system is subject to wear and premature failure due to friction and debris particle build-up.

None of the prior art provides for a combination of elements forming a collapsible, rotatable and expandable spinal hydraulic prosthetic device including a flexible metallic bellows which prevents shear-movement in a lateral direction. Additionally, none of the prior art Patents provide for a spinal implant device having a bellows/roller-bearing combination which is rotatable, thus allowing full articulation, between the two vertebrae.

SUMMARY OF THE INVENTION

The present invention provides for a collapsible, rotatable and expandable spinal hydraulic prosthetic device which is adapted to be implanted between two vertebrae. The spinal prosthetic device includes a flexible bellows positioned between two roller-bearing assemblies. The radial-thrust bearing assemblies are affixed to vertebra engaging members, respectively, which contact and set the prosthetic device to the vertebrae. The radial-thrust bearing assemblies allow for the bellows to be rotated between the two vertebrae, allowing for rotational articulated movement within the spine.

Further, the bellows is formed from a plurality of rigid washer-like members which prevent shear-movement along a lateral direction. The bellows is filled with a non-compressible fluid and may be adjusted to the desired height either pre-insertion or in vivo.

It is a principle objective of the subject collapsible, rotatable and expandable spinal hydraulic prosthetic device to provide a spinal prosthesis for replacement of a spinal disk.

It is a further objective of the subject spinal prosthetic device to provide a spinal prosthesis having an adjustable axial height.

It is a further objective of the subject invention to provide a spinal prosthesis which rotates between the two adjacent vertebrae.

It is a further objective of the subject invention concept to provide a spinal prosthetic device which prevents shear-movement along a lateral direction.

It is an important objective of the present invention to provide a spinal prosthetic device having a valve assembly allowing for the variable filling of the prosthesis with a mixture of incompressible and compressible fluids, thus allowing for a variable height of the prosthesis between the two vertebrae and also allowing for variable axial compression-movement within the prosthetic segment.

It is a further objective of the present invention to provide a spinal prosthetic device having load bearing capability afforded via a bellows configurational device.

It is an objective of the present invention to provide a spinal prosthetic device having a liquid filled metallic washer convoluted design to permit flexural movement but resist parallel shear movement.

It is a further objective of the present invention to provide a metallic bellows which affords flexing of the convolution elements which mimic natural body movements.

It is an objective of the present invention to provide a bellows design permitting axial height adjustment either pre or post implantation which can be adjusted to precisely fit the patient's intravertebral space requirement.

It is a further objective of the present spinal implant to provide an extension hose which allows for post operative intravertebral gap adjustments.

It is an additional objective of the present invention to provide a device which can be implanted in the space formerly occupied by the nucleus pulposis whereby the annulus fibrosis is left intact.

It is a further objective of the present spinal implant device to provide a system which can be substituted in place of the entire anatomical disc.

It is an important objective of the present invention to provide a spinal implant with a virtually infinite life expectancy and with no chance of rejection by the body.

BRIEF DESCRIPTION OF THE DRAWINGS

FIG. 2b is a cross-sectional side view of the subject spinal prosthetic device;

FIG. 2c is a side view of extension tubing used in conjunction with the spinal prosthetic device;

FIG. 2d is a cross-sectional view of a charge fitting device used in conjunction with the spinal prosthetic device;

DESCRIPTION OF THE PREFERRED EMBODIMENTS

Figure 1A:
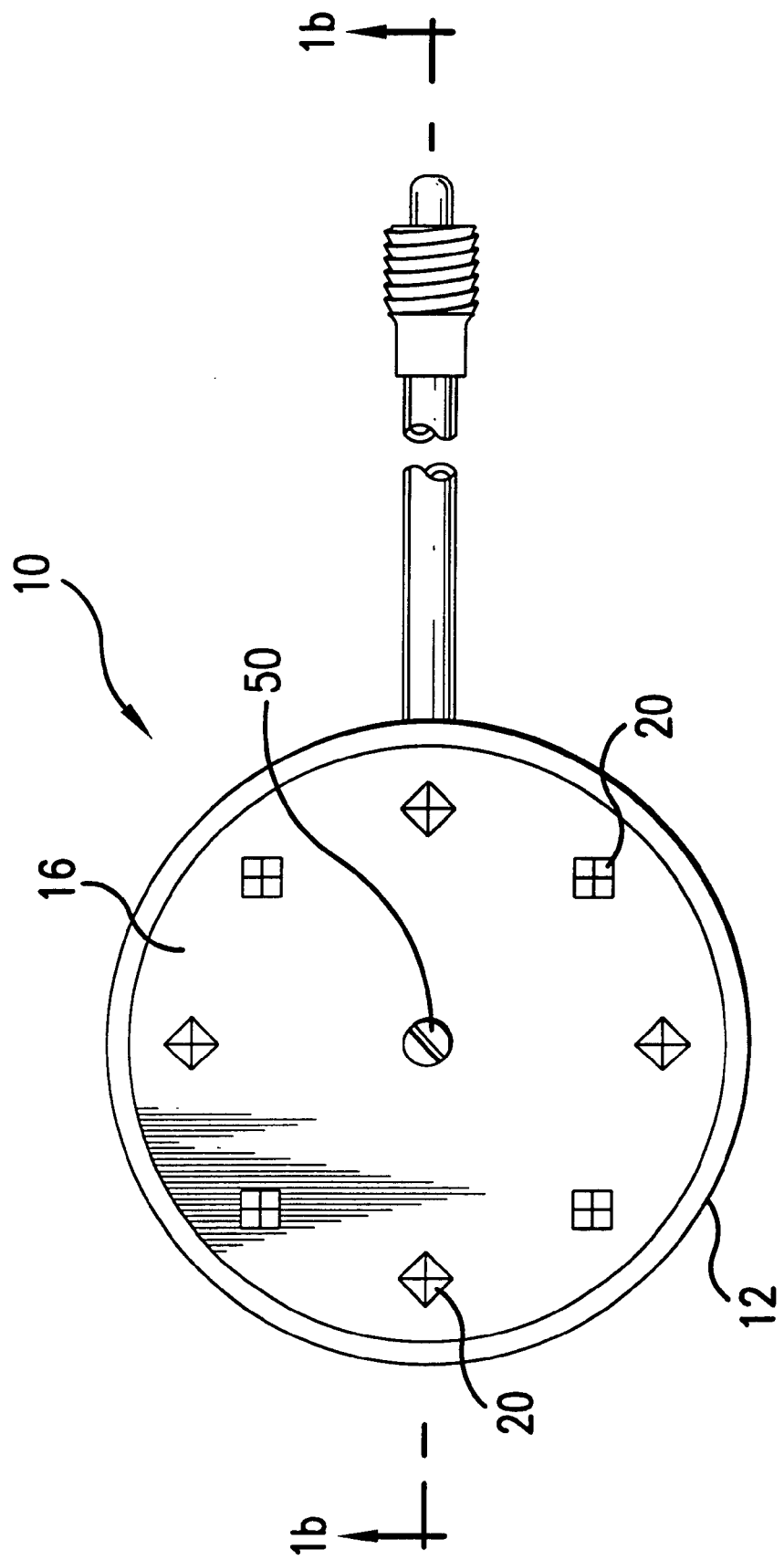
FIG. 1a is a top view of the subject spinal prosthetic device.
Figure 1B:
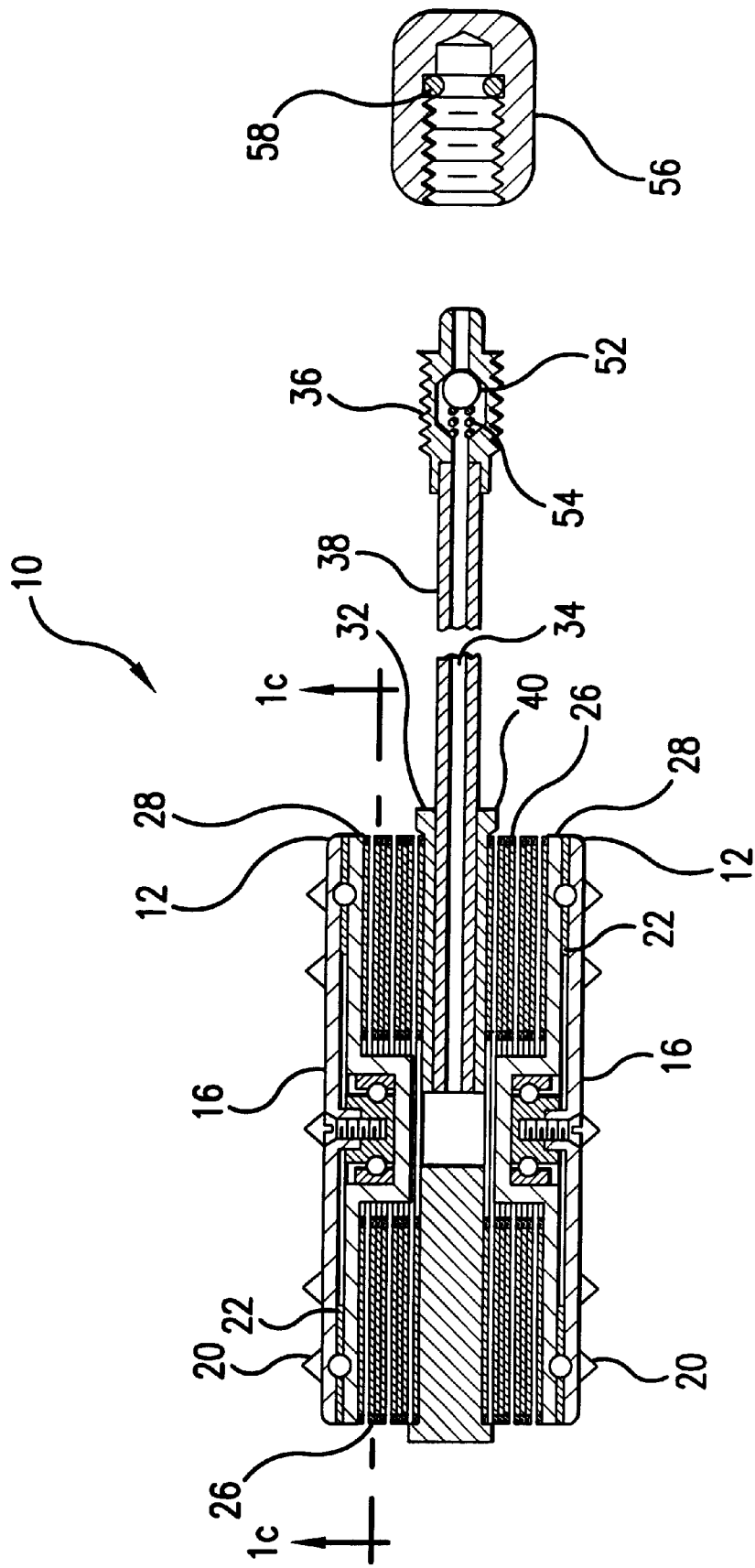
FIG. 1b is a cross-sectional view of the subject spinal prosthetic device.
Figure 1C:
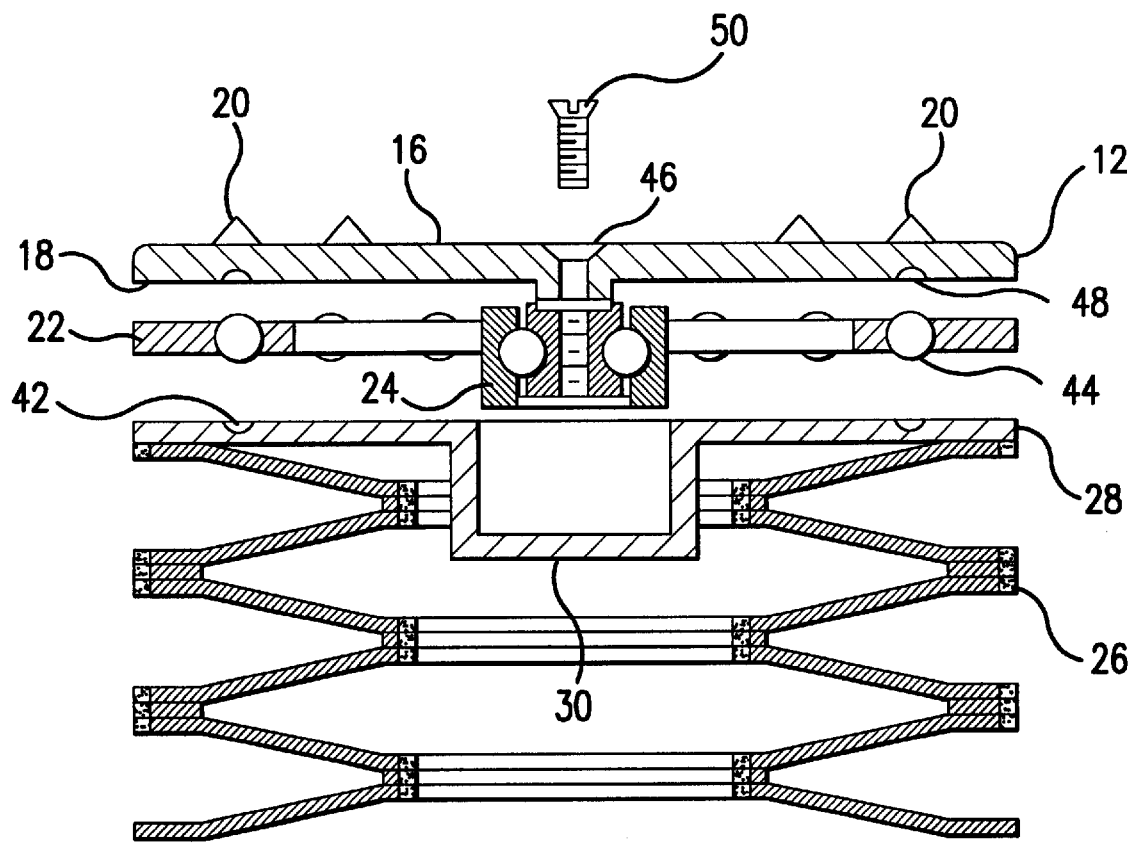
FIG. 1c is an exploded view of the top half of the subject spinal prosthetic device.

Referring now to FIGS. 1a–1c, there is shown a collapsible, rotatable and expandable spinal hydraulic prosthetic device 10. As shown in FIG. 1b, the prosthetic device 10 includes a pair of collapsible, expandable bellows 26, a pair of first vertebra engaging members 12 and a base plate member 32 having a fluid channel 34 formed therethrough.

Figure 2A:
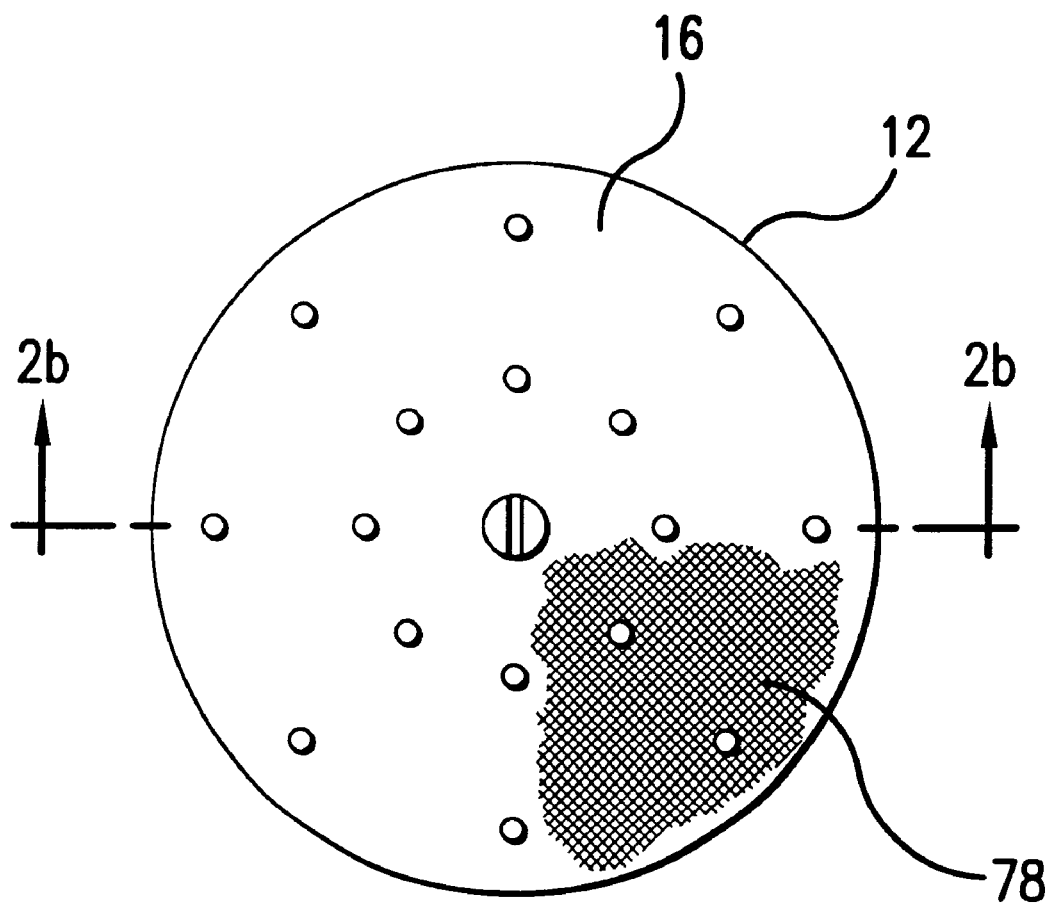
FIG. 2a is a top view of the preferred embodiment of the spinal prosthetic device.

Base plate member 32 incorporates a means for filling and bleeding fluids into or out of the assembly. The valve connector 36 can be incorporated within the base plate, as shown in the embodiment of FIG. 2b, or remotely, as shown in FIG. 1b. As shown, a capillary tube 38 fluidly connects valve connector 36 with base plate member 32. The capillary tube 38 may be formed from either ductile titanium metal or may be replaced by a flexible braid reinforced silicone rubber tube, as shown in FIG. 2c of the Drawings.

As shown in FIG. 1a, the vertebra engaging members 12 are substantially circular and may incorporate a layer of sintered titanium on upper vertebra engaging surface 16. The first vertebra engaging surface 16 has a plurality of projections 20 projecting therefrom. The projections, or spikes, 20 laterally affix or set the vertebra engaging members 12 to their respective vertebrae.

Figure 3:
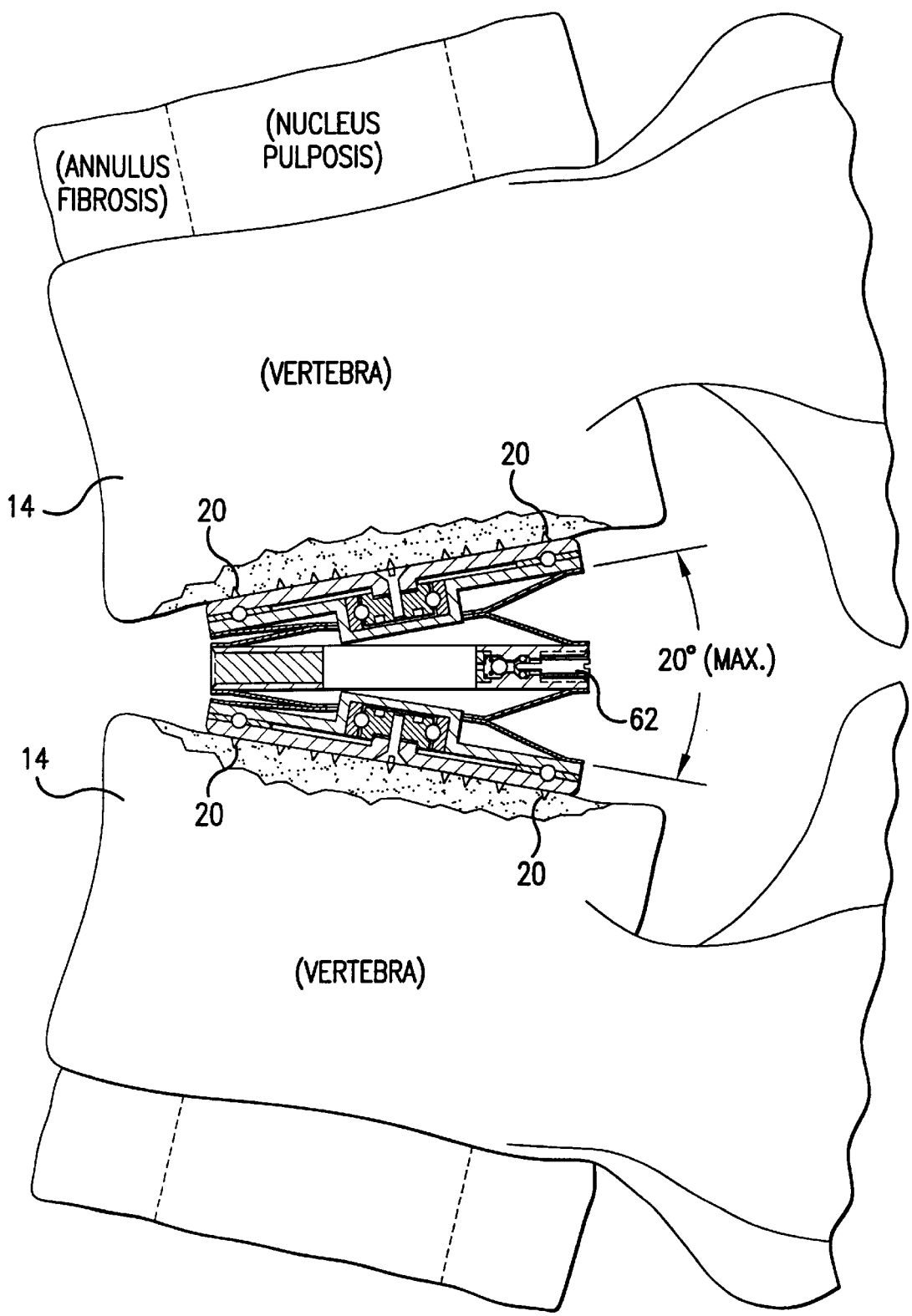
FIG. 3 is a cross-sectional side view of the spinal prosthetic device implanted between two vertebrae.

The projections or spikes 20 are shown in FIGS. 1B, 1C, and 2B as having a triangular cross-section. The spikes 20 may be of any suitable size or shape for engaging the vertebra 14, as shown in FIG. 3.

The spikes 20 may be formed from sintered titanium, solid titanium, or any other suitable material providing biocompatibility and both compressive and shear strength. Due to the fact that the spinal cord is especially sensitive to injury and damage, it is necessary that the spikes 20, as well as the other elements forming the spinal prosthetic device 10, such as the base plate member 32 and the collapsible bellows 26, be formed from strong, resilient and biocompatible materials such as titanium and other like metals or plastics compositions. Sintered titanium, for example, allows for longevity, strength, and no potential for rejection of the elements forming the spinal prosthetic device 10 by the body. Further, a prosthetic element formed from sintered titanium promotes bone growth in and around the element.

FIG. 1b is a cross-sectional view of the spinal prosthetic device 10, taken along line 1b of FIG. 1a. As shown in FIG. 1b, the base plate member 32 includes a pair of opposing outer planar surfaces 40 to which the pair of flexible bellows 26 are fixedly secured. The flexible bellows 26 are formed from a plurality of titanium washers securely joined together through laser welding, electron beam welding, resistance welding, or some other suitable method. Similarly, the flexible bellows 26 may be joined to the outer planar surfaces 40 of base plate member 32 through laser welding, electron beam welding, or any other suitable method.

The plurality of titanium washers forming the flexible bellows 26 allow for vertical flexibility and collapsibility/extendability of the bellows and also act to prevent lateral movement of the bellows. The sensitivity of the spinal cord to damage requires that the spinal prosthetic device 10 be both flexible along the main vertical axis and resistant to lateral shear movement; i.e., movement that would bend the bellows into a parallelogram shape. A rocking motion of the prosthetic device 10 is desired for natural movement.

As shown in FIG. 1c, the collapsible bellows 26 are sealed on one end by end cap 28. End cap 28 may be made of titanium or any other suitable, strong and rigid metal material, which is weld compatible with bellows 26. End cap 28 is bonded to collapsible, extendible bellows 26 through welding or any other suitable means. As shown, end cap 28 is formed with bearing recess 30 formed therein. Additionally, end cap 28 has an annular groove 42 formed therein.

Thrust bearing member 22, as best shown in FIG. 1c, incorporates multiple hardened steel ball bearings captured within a biocompatible washer seal material. As shown in FIGS. 1b and 1c, a radial bearing assembly 24 is positioned in the center of the substantially annular thrust bearing member 22. The radial bearing assembly 24 is received within the bearing recess 30 of end cap 28. The ball bearing projections of the thrust bearing member 22 are received within the annular groove 42 formed on the end cap 28.

The vertebra engaging member 12 incorporates a sintered titanium planar surface 16 with projections 20 projecting therefrom. Opposite upper surface 16 is lower surface 18 which has an annular groove formed therein. The vertebra engaging members 12 each have a through hole 46 formed through the center of the annular plate.

Ball bearing members 44 of thrust bearing member 22 are received within the annular groove 48 of the vertebra engaging member 12. The vertebra engaging member 12 is fixed to the thrust bearing member 22 by screw 50, which is received within the radial bearing assembly 24.

When the vertebra engaging members 12, the thrust bearing members 22, and the collapsible, extendible bellows 26 are assembled, as shown in FIG. 1b, the collapsible, extendable bellows and the base plate member 32 are free to rotate with respect to the vertebra engaging members 12. FIG. 3 illustrates the spinal prosthetic device 10 implanted between two vertebrae 14. The prosthetic device 10 may replace an entire diseased spinal disc or it may be positioned within the nucleus pulposis space of a spinal disc wherein the nucleus pulposis material is removed.

As shown in FIG. 3, projections 20 engage the bone of the vertebrae, holding the spinal prosthetic device in place with respect to the spine. The rotation of the collapsible, extendable bellows 26 and the base plate member 32 with respect to the vertebra engaging members 12 allows for a fully rotating and articulating motion of the prosthetic device 10 with respect to the adjoining vertebrae 14. Thus, the spinal prosthetic device 10 provides for natural movement of the spine.

A silicone grease or other biocompatible lubricant may be present on either surface of the thrust bearing member 22 in order to add lubrication to end cap 28 and vertebra engaging member 12 with respect to the thrust bearing member 22. In order to provide full articulated movement within the spine, it is necessary that the collapsible, extendable bellows 26 be rotatable with respect to the two vertebrae 14. This rotation provides both natural rotating movement of the spine and also decreases the risk of injury and dislocation of the vertebra engaging members 12 with respect to the vertebrae 14.

As shown in FIG. 1b, valve connector 36 is provided with an outer thread and includes ball check 52 which is biased in the closed position by spring 54. End cap 56 is provided as a back-up sealing means after all filling adjustments have been completed. End cap 56 has a threaded recess formed therein for receiving the threads of valve connector 36. Also received within the recess of end cap 56 is an O-ring seal 58.

Valve connector 36 is provided for the filling of the collapsible, extendable bellows 26 with either an incompressible liquid or a mixture of a liquid and a gas. Fluid flows through fluid channel 34 of capillary tube 38 to fill the bellows assembly 26 to a predetermined height, depending upon the desired intervertebral spacing.

FIG. 2b shows the preferred embodiment of the spinal prosthetic device 10. Valve connector 36 is integral with base plate member 32, as shown. Further, the bellows assembly 26 are each comprised of two conical washers formed of titanium or like composition. This configuration is pre-expanded to approximate the final desired gap between the vertebrae 14 and relies on the surgeon to distract the vertebrae with a distractor tool prior to implantation of the device. The device can be sized to fit into the space formerly occupied by the nucleus pulposis when the annulus fibrosus is left intact or sized with a larger diameter to fit between the vertebrae 14 when the annulus fibrosus has been removed. Using only four or fewer flexible Belleville type washers, as shown in FIG. 2b, the total number of degrees of bending are limited to approximately 20°, which approximates normal spinal disk movement.

FIG. 2d illustrates a charge fitting 60 adapted for use with valve 36. Charge fitting 60 is received within valve connector 36. The charge fitting includes a hypodermic needle 64 which passes through O-ring seal 58, effecting a seal. As the fitting 60 is further inserted into valve connector 36, needle 64 pushes the ball check 52 away from its seat and further compresses the spring behind it.

Once the ball check 52 is unseated, liquid or gas may be pumped into the device, causing it to expand. When the surgeon wishes to detract the device, the relief knob on the pump (not shown) is opened and the liquid or gas will bleed back into the pump.

FIG. 2c illustrates extension tubing 68. Extension connector 66 is received within valve connector 36, allowing remote valve connector 36' to be used in place of the valve connector 36. Thus, the prosthetic device 10 may be filled with liquid and gas either through the valve positioned on the base plate member 32 or through the remote extension tubing 68. Extension tubing 68 is preferable for filling and bleeding of fluids from the collapsible, extendable bellows 26 when the spinal prosthetic device 10 has already been implanted within the spine of the patient.

When the final gap setting has been achieved, the surgeon unscrews the charge fitting 60 and, as needle 64 withdraws, the ball check 52 closes, effecting a seal before the needle 64 passes out beyond O-ring 58. In order to make the final seal, the surgeon screws plug 62 into the valve connector 36, or the remote valve connector 36' if the extension tubing 68 is employed.

FIG. 3 illustrates the preferred embodiment of the spinal prosthetic device 10, shown in FIG. 2b, implanted in the lumbar region of the spine. The device is shown tilted to its maximum of approximately 20° which may be varied to suit. The device is shown as it would be situated if the annulus fibrosus were completely removed. A smaller diameter version of this device configuration similar to FIG. 1 or 2 may be similarly implanted within the space formerly occupied by the nucleus pulposus, wherein the annulus fibrosus is left intact.

Figure 4A:
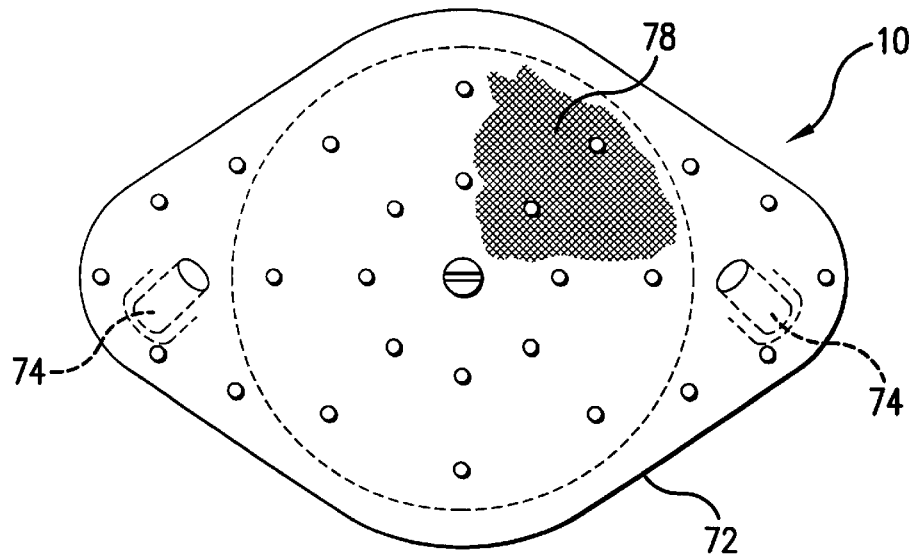
FIG. 4a is a top view of an alternate embodiment of the spinal prosthetic device.
Figure 4B:
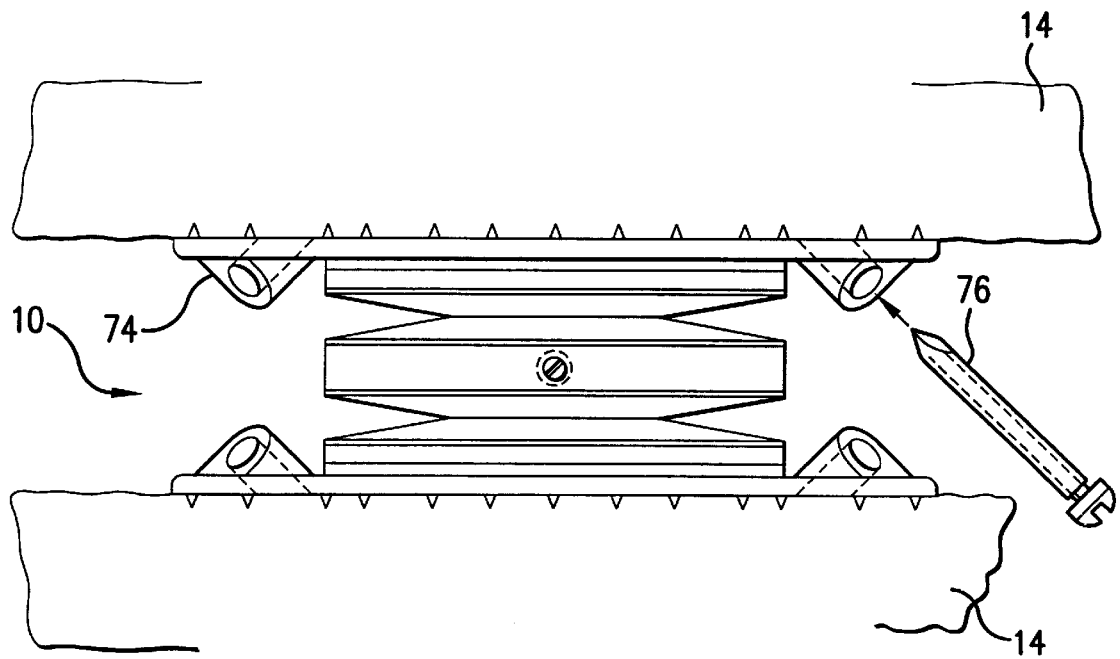
FIG. 4b is a side view of the alternate embodiment of the spinal prosthetic device; and, FIG. 5 is a graph showing a typical Stress vs. Strain curve for a typical metal material.

FIG. 4a is a top view of the spinal prosethetic device 10 with expanded vertebra engaging members 72. The vertebra engaging members 72 have been modified in this embodiment to incorporate bores 74 for receiving screws 76, illustrated in FIG. 4b. The self-taping screws 76 can be used to secure the expanded vertebra engaging members 72 to their cojoining vertebrae. The surgeon, with the use of a separate drill insert bushing, can use the bores 74 to first pre-drill a screw diameter hole into the vertebrae prior to installing the self-taping screw 76. This configuration can be used when the annulus fibrosus has been removed. The screws 76 provide further stability and strength for implantation of the spinal prosthetic device 10. The screws 76 may be used in conjunction with projections 20, as shown in FIG. 4b.

Further shown in FIG. 4a is irregular surface 78. The porous surface 78 forms a mesh or sintered surface for allowing vetebra engaging members 72 to easily join to the vertebrae. In addition to the screws 76, the vetebra engaging members 72 are held to the bone of the vetebrae by actual growth of the bone into the porous surface 78. A porous surface 78 is also formed on the vertebra engaging members 12 of the embodiment shown in FIG. 2a.

Figure 5:
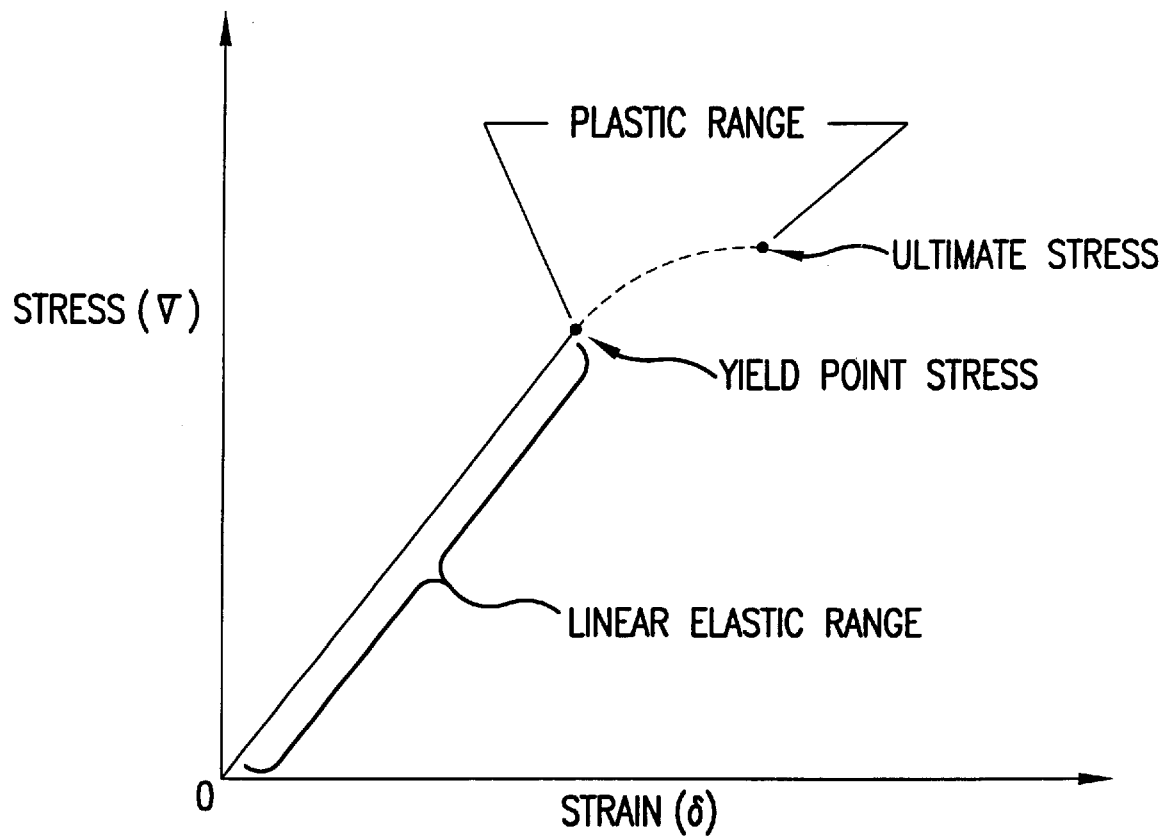

FIG. 5 shows a typical Stress vs. Strain curve showing the behavior of most metal materials. The spinal prosthetic device 10 is designed such that the maximum anticipated load, with a built-in factor of safety, would never exceed the yield point stress allowed for the materials of construction.

FIG. 5 is a typical graph of the Stress vs. Strain or the Stress vs. Deflection of most metal materials. The linear portion of the curve defines what is commonly called the "elastic" portion. If the applied stress never exceeds the linear part of the curve, once the stress is removed, the material will revert back to its original shape. If the stress exceeds the "yield" point for the material, then "plastic" deformation occurs and the material will not revert back to its original shape. If the stress level increases to the "ultimate" value, the material will fail as a support.

The collapsible, extendable bellows 26 are designed such that the "yield point" is never reached and, theoretically, an infinite number of compression/extension and bending cycles can be expected. In bellows systems utilizing Belleville type conical washers made of titanium, hundreds of millions of cycles are routinely imposed without failure. The bellows design incorporates the torsional stability of a coil spring with the tension and compression stability of a leaf spring. Regardless of how the loads are applied, deflection is effected without parts destructively rubbing against one another.

Further, the bellows assembly 26 offers both spring-like action while also lending itself as a container to house a fluid. If this fluid is an incompressible liquid, the bellows will only tilt laterally, not deflect axially. If partially filled with both a gas and a liquid, some axial deflection, as well, will be afforded due to the compressibility of the gaseous portion.

The bellows assembly 26 allow forward, backward and lateral motion within the spine while maintaining axial height rigidity due to the incompressibility of the liquid contained therein. The bellows 26 absorbs the imposed stresses via bending of its convolutions. There is no rubbing of one component against another, thus eliminating wear on the mechanical parts.

In order to afford a torsional degree of motion, simulating natural spinal movement, between the cojoining vertebrae, the upper and lower vertebra engaging members 12 roll on ball bearings 44. There is virtually no friction, heat or wear produced in the rolling contact between the vertebra engaging members 12 and the ball bearings 44 as long as the yield stress of neither the ball bearing 44 nor the race 48 or 28 is exceeded.

The device may be sized so as to make it adaptable to fit in other regions of the spine, such as the cervical and thoracic regions. Just as the cross-sections of the vertebrae increase in area from the cervical region down to the sacrum, the normal loading encountered increases proportionally. Thus, it follows that the larger the cross-sectional area of the bellows 26, the lower the imposed stresses will be on the bellows convolutions. The bearing load imposed between the vertebra engaging members 12 and the vertebrae 14 will also be lower.

Titanium which is the preferred metal, is not only biocompatible, it is one of the strongest metals available. It lends itself to handling the pressures and flex-loading stresses encountered in a bellows configuration design.

The spinal prosthetic device 10 may be pre-filled with sterile saline solution at the time of manufacture. The device may, alternatively, be filled with 80%–90% liquid, the remaining volume being gas. This would allow the device to afford some spring action in the axial direction similar to a normal vertebral disk. Alternatively, the bellows 26 may be pre-expanded to be near the final height desired and, in this embodiment, the surgeon would use a separate distracting tool to spread the effected vertebrae apart before inserting the device 10 into final position.

If the surgeon needs to adjust the height of the device 10, he or she may connect a hand pump to the fill/drain fitting 36 of the device 10 and either bleed fluid out or pump extra fluid in.

In cases where the surgeon desires to keep the annulus fibrosus intact, but cannot distract the vertebrae to their final position at the time of the surgery, the surgeon can attach a short length of capillary braid reinforced tubing 68, shown in FIG. 2C, to the bellows device 10 and tuck the entire tubing extension 68 inside the incision prior to closing the patient up.

After a predetermined time, the patient may have an incision formed on an adjacent area of the back. The tubing 68 can be removed for expanding the bellows 10 to the final gap height desired. This could be performed with the aid of real time fluoroscopy.

The radial bearing assembly 24 positioned centrally within the thrust bearing member 22 allows for rotation of the bellows with respect to the vertebra engaging members 12. Thus, spinal prosthetic device 10 provides lateral tilting, minimal axial compression, and permits rotational movement, thus simulating a natural spinal disk.

Further, the individual washers forming the flexible bellows 26 provide for not only flexibility along the main axis of the spinal prosthetic device 10, but prevent shear movement in the radial direction. The spinal cord is especially susceptible to injury and damage, and the liquid hydraulic fluid within the bellows assembly 26 prevents the device from being crushed or shifted in the radial direction, thus preventing injury to the sensitive nerves of the spinal cord or aorta.

Although this invention has been described in connection with specific forms and embodiments thereof, it will be appreciated that various modifications other than those discussed above may be resorted to without departing from the spirit or scope of the invention. For example, functionally equivalent elements may be substituted for those specifically shown and described without departing from the spirit or scope of the invention as defined in the appended claims.

What claimed is:

1. A collapsible, rotatable and expandable spinal hydraulic prosthetic device comprising:
    a pair of opposed vertebra engaging members, each having a first vertebra engaging surface for joining said vertebra engaging member to a vertebra and having a second bearing surface;
    a pair of thrust bearing members, each having a radial bearing assembly, said pair of radial bearing assemblies being fixedly secured to said vertebra engaging members, each of said members being contiguous and rotatable with respect to said second bearing surfaces;
    a pair of collapsible, extendable bellows, each having an end cap formed on a first end thereof, said end cap having a bearing recess formed therein, said bearing recess receiving said radial bearing assembly of said thrust bearing member, said thrust bearing member being contiguous and rotatable with respect to said end cap; and, a base plate member having opposed annular surfaces, each of said annular surfaces being fixedly secured to a second end of said collapsible, extendable bellows, said base plate member having a fluid channel formed therethrough for allowing said bellows to be filled with a fluid.

2. The collapsible, rotatable and expandable spinal hydraulic prosthetic device as recited in claim 1 wherein said second bearing surface of each of said vertebra engaging members has an annular groove formed therein.

3. The collapsible, rotatable and expandable spinal hydraulic prosthetic device as recited in claim 2 wherein said pair of thrust bearing members each have a plurality of ball bearings annularly positioned thereon and received within said annular groove of said second bearing surface.

4. The collapsible, rotatable and expandable spinal hydraulic prosthetic device as recited in claim 3 wherein each of said end caps has an end cap annular groove formed thereon for receiving said plurality of ball bearings.

5. The collapsible, rotatable and expandable spinal hydraulic prosthetic device as recited in claim 1 wherein said fluid is an incompressible fluid.

6. The collapsible, rotatable and expandable spinal hydraulic prosthetic device as recited in claim 1 wherein each of said first vertebra engaging surfaces includes a plurality of engaging members projecting therefrom for securing said pair of vertebra engaging members to a pair of vertebrae.

7. The collapsible, rotatable and expandable spinal hydraulic prosthetic device as recited in claim 1 wherein each of said pair of opposed vertebra engaging members has a plurality of fixing openings formed therethrough for receiving a plurality of securing members to secure said vertebra engaging members to said vertebrae.

8. The collapsible, rotatable and expandable spinal hydraulic prosthetic device as recited in claim 1 wherein each of said pair of collapsible, extendable bellows is formed from a plurality of washer members joined each to the other.

9. The collapsible, rotatable and expandable spinal hydraulic prosthetic device as recited in claim 1 wherein said fluid is a combination of compressible and incompressible fluids.

10. The collapsible, rotatable and expandable spinal hydraulic prosthetic device as recited in claim 1 wherein said fluid is a mixture of incompressible and compressible fluids.

11. The collapsible, rotatable and expandable spinal hydraulic prosthetic device as recited in claim 1 wherein said base plate member includes a valve member in fluid communication with said fluid channel for selectively sealing said fluid channel.

12. The collapsible, rotatable and expandable spinal hydraulic prosthetic device as recited in claim 1 wherein an extension hose is coupled with said base plate member for fluid adjustment of said pair of collapsible, extendable bellows.

13. A collapsible, rotatable and expandable spinal hydraulic prosthetic device comprising:

a pair of opposed vertebra engaging members, each having a first vertebra engaging surface for joining said vertebra engaging member to a vertebra, each of said vertebra engaging members having a second bearing surface;

a pair of thrust bearing members, each of said thrust bearing members including a radial bearing assembly, said pair of radial bearing assemblies being fixedly secured to said vertebra engaging members, each of said thrust bearing members being contiguous and rotatable with respect to said second bearing surfaces;

a pair of collapsible, extendable bellows, each having an end cap formed on a first end thereof, said end cap having a bearing recess formed therein, said bearing recess receiving said radial bearing assembly of said thrust bearing member, said thrust bearing member being contiguous and rotatable with respect to said end cap; and, a base plate member including opposing annular surfaces, each of said annular surfaces being fixedly secured to a second end of said collapsible, extendable bellows, said base plate member having a fluid channel formed therethrough for permitting said bellows to be filled or unfilled with a fluid, said fluid channel being in fluid communication with a valve assembly.

14. The collapsible, rotatable and expandable spinal hydraulic prosthetic device as recited in claim 13 wherein said second bearing surface of each of said vertebra engaging members includes an annular groove formed therein.

15. The collapsible, rotatable and expandable spinal hydraulic prosthetic device as recited in claim 14 wherein said pair of thrust bearing members each include a plurality of ball bearings annularly positioned thereon and received within said annular groove of said second bearing surface.

16. The collapsible, rotatable and expandable spinal hydraulic prosthetic device as recited in claim 15 wherein each of said end caps has an end cap annular groove formed therein for receiving said plurality of ball bearings.

17. The collapsible, rotatable and expandable spinal hydraulic prosthetic device as recited in claim 13 wherein said fluid is an incompressible fluid.

18. The collapsible, rotatable and expandable spinal hydraulic prosthetic device as recited in claim 13 wherein each of said first vertebra engaging surfaces includes a plurality of engaging members projecting therefrom for securing said pair of vertebra engaging members to a pair of vertebrae.

19. The collapsible, rotatable and expandable spinal hydraulic prosthetic device as recited in claim 13 wherein each of said pair of opposed vertebra engaging members includes a plurality of fixing openings formed therethrough for receiving a plurality of securing members to secure said vertebra engaging members to said vertebrae.

20. The collapsible, rotatable and expandable spinal hydraulic prosthetic device as recited in claim 13 wherein each of said pair of collapsible, extendable bellows is formed from a plurality of washer members joined each to the other.

21. The collapsible, rotatable and expandable spinal hydraulic prosthetic device as recited in claim 13 wherein said fluid is a mixture of incompressible and compressible fluids.

22. The collapsible, rotatable and expandable spinal hydraulic prosthetic device as recited in claim 13 wherein said valve assembly is positioned remotely from said base plate member.

23. The collapsible, rotatable and expandable spinal hydraulic prosthetic device as recited in claim 22 wherein said valve assembly is fluidly connected to said base plate member by an extension hose.

24. The collapsible, rotatable and expandable spinal hydraulic prosthetic device as recited in claim 13 wherein said fluid is a combination of compressible and incompressible fluids.

25. The collapsible, rotatable and expandable spinal hydraulic prosthetic device as recited in claim 13 wherein adjacent vertebrae are adjustably distracted by selective in situ hydraulic filling of said pair of collapsible, expandable bellows.

26. The collapsible, rotatable and expandable spinal hydraulic prosthetic device as recited in claim 13 wherein said device is implanted within the space formerly occupied by the nucleus pulposis of said spinal disc, leaving the annulus fibrosis intact.

27. The collapsible, rotatable and expandable spinal hydraulic prosthetic device as recited in claim 13 wherein said device replaces entirely said spinal disc when the annulus fibrosis of said spinal disc is removed.

* * * * *